United States Patent [19]
Sohn et al.

[11] Patent Number: 6,106,702
[45] Date of Patent: Aug. 22, 2000

[54] OLEFINIC HYDROCARBON SEPARATION PROCESS

[75] Inventors: Stephen W. Sohn, Arlington Heights; Santi Kulprathipanja, Inverness, both of Ill.

[73] Assignee: UOP LLC, Des Plaines, Ill.

[21] Appl. No.: 09/222,149

[22] Filed: Dec. 29, 1998

[51] Int. Cl.[7] .............................. C07C 7/13; C07C 7/00; C07C 7/12; C10G 25/03; C10G 25/12

[52] U.S. Cl. ................. 208/310 Z; 585/802; 585/809; 585/820; 585/822; 585/826; 585/827; 585/829

[58] Field of Search ..................... 585/820, 826, 585/827, 829, 822, 802, 809; 208/310 Z

[56] References Cited

U.S. PATENT DOCUMENTS

| | | | |
|---|---|---|---|
| 3,510,423 | 5/1970 | Neuzil et al. | 208/310 |
| 4,006,197 | 2/1977 | Bieser | 260/676 |
| 4,899,016 | 2/1990 | Clark et al. | 585/826 |
| 5,276,246 | 1/1994 | McCulloch et al. | 585/829 |
| 5,300,715 | 4/1994 | Vora | 585/254 |

OTHER PUBLICATIONS

*Olex: A Process for Producing High Purity Olefins* presented by J.A. Johnson, S. Raghuram and P.R. Pujado at the Aug. 1987 Summer national meeting of the American Institute of Chemical Engineers in Minneapolis, Minnesota.

*Primary Examiner*—Walter D. Griffin
*Assistant Examiner*—Tam M. Nguyen
*Attorney, Agent, or Firm*—John G. Tolomei; John F. Spears, Jr.

[57] ABSTRACT

A molecular sieve guard bed used in an adsorptive process for separating olefinic hydrocarbons from paraffinic hydrocarbons is regenerated in a method which recovers valuable hydrocarbons from the guard bed void volumes. The method comprises first contacting the sieve with a purge stream, with the initial effluent of the guard bed passed into a raffinate column to recover the olefinic hydrocarbons in the void volume of the bed. The flow of the effluent of the guard bed is then switched to a different fractionation column.

12 Claims, 1 Drawing Sheet

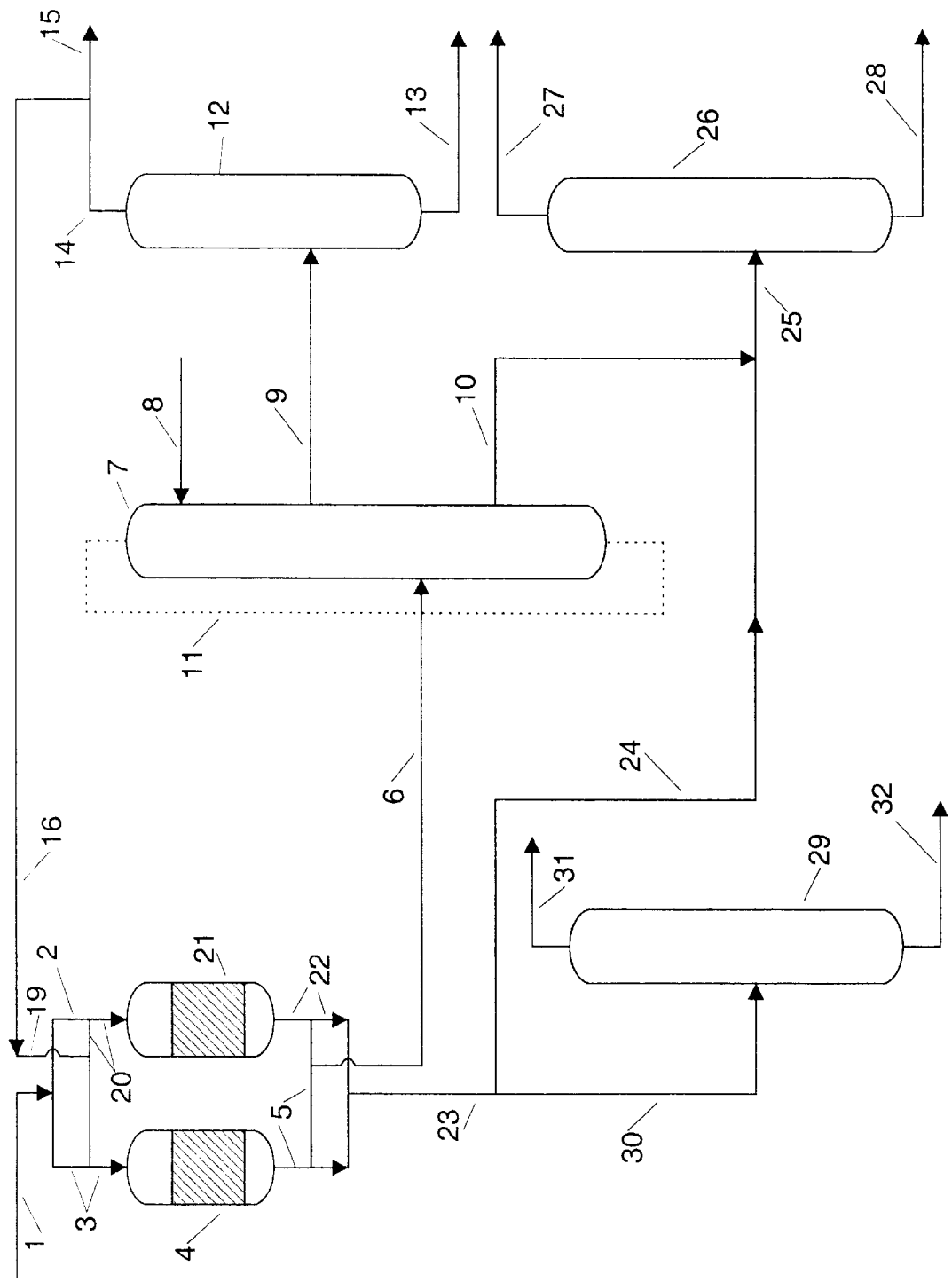

OLEFINIC HYDROCARBON SEPARATION PROCESS

FIELD OF THE INVENTION

The invention relates to a process for the adsorptive separation of hydrocarbons from a feed mixture comprising the hydrocarbons and a different type of hydrocarbons such as the separation of olefins from paraffins. The invention more specifically relates to a method for the regeneration of a molecular sieve used as a guard bed in this chemical separation process.

RELATED ART

Molecular sieves are widely used to separate hydrocarbons. For instance, it is known in the art that adsorptive separation using a molecular sieve adsorbent is an effective method to separate linear olefinic hydrocarbons from a feed mixture comprising the linear olefinic hydrocarbons and another class of hydrocarbons having a similar volatility such as paraffins or nonlinear olefins of the same general molecular weight. This process is described in a paper entitled *Olex: A Process for Producing High Purity Olefins* presented by J. A. Johnson, S. Raghuram and P. R. Pujado at the August 1987 Summer national meeting of the American Institute of Chemical Engineers in Minneapolis, Minn. This paper describes a simulated moving bed (SMB) countercurrent adsorptive separation process for the separation of light straight-chain olefins from similar paraffins. A similar but more detailed description of a simulated moving process for the separation of linear olefins is provided in U.S. Pat. No. 3,510,423 issued to R. W. Neuzil et al.

U.S. Pat. No. 5,276,246 issued to B. McCulloch et al. describes a process for the adsorptive separation of normal olefins from a mixture of normal olefins and branched chain olefins using a low acidity silica molecular sieve such as a silicalite or ZSM molecular sieve.

U.S. Pat. No. 5,300,715 issued to B. V. Vora describes an overall process for the conversion of paraffins to olefins. The process includes dehydrogenation of the paraffins and adsorptive separation of the olefins from a paraffin/olefin mixture recovered from the effluent of the dehydrogenation zone. The patent describes a zone used to selectively remove aromatic hydrocarbons from the paraffin/olefin mixture to prevent the aromatic hydrocarbons from deactivating a molecular sieve used in the adsorptive separation of the paraffin/olefin mixture. The removal of the aromatics also aids the performance of the dehydrogenation zone of the process. The aromatics removal zone is taught as possibly containing a molecular sieve, which is regenerated as needed.

U.S. Pat. No. 4,006,197 issued to H. J. Bieser is pertinent for its showing of the raffinate and extract columns normally employed to separate these streams discharged from the SMB adsorption zone and to thereby recover desorbent for recycling within the process. Although not directed to the separation of linear olefins, the overall flow of the process is similar to that employed in the subject process.

BRIEF SUMMARY OF THE INVENTION

The invention is a process for separating olefins from paraffins by adsorptive separation characterized by the method used to regenerate a molecular sieve guard bed employed to remove aromatic hydrocarbon contaminants from the feed stream of the process. Use of an existing internal stream as the flush and regenerant material allows integration of the regeneration into the preferred separation process eliminating the need for outside fluids while also allowing for the facile recovery of regenerant and displaced feed components. One embodiment of the invention may be characterized as a process for the separation of a first hydrocarbon from a feed stream comprising the first hydrocarbon and at least one other hydrocarbon, which process comprises periodically regenerating a molecular sieve guard bed used in the process by purging the feed stream from the guard bed using a stream of a desorbent used in the separation process and passing the effluent of the guard bed into a fractionation column used in the process to separate the desorbent and raffinate compounds, and then continuing to pass a stream of the desorbent through the guard bed but directing the effluent of the guard bed to a desorbent recovery fractionation column.

BRIEF DESCRIPTION OF THE DRAWING

The Drawing is simplified process flow diagram showing parallel guard beds 4 and 21 upstream of an adsorption chamber 7 and also showing the fractionation columns 12, 26 and 29 employed in the process.

DETAILED DESCRIPTION AND PREFERRED EMBODIMENTS

Olefinic hydrocarbons are very useful chemical compounds. They are reacted with themselves to form polymers or with other molecules in alkylation reactions in both the petrochemical and petroleum refining industries to make a wide variety of chemical products. It is often necessary for the olefins to be relatively high in purity in order to most effectively employ the olefins or to minimize by product formation. At other times it is undesirable to have non olefinic hydrocarbons present in an olefin containing stream due to their formation of undesired by-products. In both instances it is necessary or at least desired to separate the olefins from nonolefinic hydrocarbons such as paraffins. In other instances the desired olefin is just one particular type of olefin such as a normal olefin or alpha olefin which is present in a mixture comprising other types of olefins such as branched olefins.

When a particular desired olefin is admixed with a chemical species of different relative volatility, the olefin is normally recovered from the admixture by the simple expedient of fractional distillation. However, in many instances the olefin is present in a mixture containing one or more different hydrocarbons having rather similar volatilities, which makes such a separation difficult or impossible by fractional distillation. One common example of this occurs when the olefins are produced by the dehydrogenation of a paraffin or a mixture of paraffins. As the dehydrogenation reaction will not proceed to completion due to equilibrium constraints, the product stream of the dehydrogenation zone is a homologous mixture of paraffins and olefins of the same general chemical structure. These compounds will have very similar boiling points and are very difficult to separate by fractional distillation. In this instance adsorptive separation is often the most economical separation method, with the separation utilizing an adsorbent which is selective for one species, such as the olefins, over the other.

The olefins recovered in the main olefin separation zone of the subject process may be either straight chain or branched olefins or both depending on the application of the process. The nonrecovered hydrocarbons in the feed stream may be a different type of olefin or paraffins or a mixture. The process may therefore be specific to the recovery of normal olefin(s) from a mixture comprising isoolefins and/or paraffins. The olefinic product may comprise a single molecule such as isopentene or a mixture, such as n-hexenes and n-heptenes. The olefinic product may also comprise a several carbon number range of homologs such as the $C_{10}$ to $C_{14}$ linear olefins desired for use in the production of linear alkyl benzenes used as a detergent precursor.

Adsorptive separation can be performed using a variety of different techniques such as swing bed operation using two or more fixed beds with adsorption and regeneration steps cycling between them, moving bed operation in which the adsorbent is transported between adsorption and desorption zones and simulated moving bed (SMB) operation, such as described in U.S. Pat. Nos. 3,510,423; 3,720,604; 3,723,302 and 3,755,153. These patents are incorporated herein for their background teaching as to simulated moving bed adsorptive separation techniques, nomenclature and for their description of adsorbents useful for adsorptive separations. Although simulated moving bed separations such as described in the above cited references are preferred, the manner in which the adsorbent is contacted with the feed stream is not a limiting factor in the subject invention. The adsorbent regeneration procedure set out herein is applicable to any of these different adsorption techniques and for any process employing suitably adaptable guard beds, desorbents and fractionation columns.

An adsorptive separation process basically comprises an adsorption step performed at adsorption conditions in which the adsorbent is brought into contact with the olefin containing feed and a desorption step in which selectively adsorbed olefins are removed from the adsorbent at desorption conditions. It is preferred that the desorption step is promoted through the contact of the adsorbent with a desorbent compound at conditions relatively similar to those employed in the adsorption step. However, the adsorbed olefins could be removed from the adsorbent by means of a change in temperature or pressure or both. That is, thermal swing adsorptive separation or pressure swing adsorptive separation could be used if desired. Pressure swing systems operate in vapor phase and the olefin separation step of the subject process may employ vapor phase adsorption and desorption conditions. These alternative desorption methods typically do not employ a desorbent, which may limit the applicability of the subject process.

The desorption step will produce a process stream containing a mixture of the desorbed olefins and the desorbent used in the process. This process stream is referred to as the extract stream preferably passed into a desorbent separation and recovery zone which allows the desorbent to be recycled within the process. This zone typically comprises a fractional distillation column referred to in the art as the extract column to recover the desorbent. The nonadsorbed components of the feed stream are removed in a process stream referred to herein as the raffinate stream. If appropriate this stream is also passed into a fractional distillation column, referred to herein as the raffinate column.

Aromatic hydrocarbons present in the feed stream to the process will collect on the preferred adsorbent used to separate normal olefins from the feed stream. This will have several deleterious effects on the performance of the process. First, the aromatic hydrocarbons will occupy active sites on the adsorbent which prevents these sites from being employed in the separation. The capacity of the sieve and therefore of the process is reduced. If the aromatics continue to build up they reach an equilibrium concentration. At this time the aromatics there will be no net collection of aromatics on the adsorbent, and they will instead pass through the adsorption zone and emerge in the extract and raffinate streams. Aromatic hydrocarbons are normally considered an impurity in the normal olefins recovered from the extract stream. Aromatic hydrocarbons present in the raffinate stream will be concentrated into the paraffins. These are often recycled to an olefin producing zone such as a dehydrogenation zone. Passage of aromatic hydrocarbons into a catalytic dehydrogenation zone is normally considered undesirable since the aromatics can alkylate with the olefins to produce byproducts. The presence of aromatics in the feed or product of a dehydrogenation zone can have other undesired effects as described in the previously cited U.S. Pat. No. 5,300,715. Therefore it is undesirable to allow the passage of aromatic hydrocarbons including benzene into the main adsorption zone.

The adsorbents employed in the subject process are preferably molecular sieves formed from inorganic oxides such as silica and alumina; that is, aluminosilicates. Such materials include the well known commercially available zeolites such as zeolite Y and zeolite X. The microcrystalline sieve structure provided by many zeolites is important in the selectivity of the adsorbent for the olefinic hydrocarbon. However, it is believed the subject invention could also be employed to regenerate an inorganic oxide material which is not a zeolite but which is used as the adsorbent in a guard bed located upstream of the main olefin separation zone. The term molecular sieve is intended to include a broad variety of inorganic oxides which are suitable as guard bed adsorbents and/or as adsorbents for the separation of olefins including the silicalite materials described in the above cited references. Silicalites are very high silica to alumina ratio molecular sieves which are not zeolites due to their lack of ion exchange capacity. Silicalites are described in greater detail in U.S. Pat. Nos. 4,061,724; 4,073,865 and 4,104,294. Another type of inorganic oxide molecular sieve which could be used in the adsorbent is the ZSM type zeolite such as disclosed in U.S. Pat. No. 3,702,886 (ZSM-5), U.S. Pat. No. 3,832,449 ( ZSM-12), U.S. Pat. No. 4,016,245 (ZSM-35) and U.S. Pat. No. 4,046,859 (ZSM-38).

The preferred adsorbent for use in the separation zone is an attrition resistant particle of about 20–40 mesh (U.S.) size formed by extrusion or spray drying an admixture of a binder such as clay or alumina and a type X or type Y zeolite. The type X zeolite is described in U.S. Pat. No. 2,822,244 and the type Y zeolite is described in U.S. Pat. No. 3,130,007. The zeolites may be ion exchanged to replace native sodium with one or more other cations selected from the alkali metals, the alkaline-earth metals and the coinage metals. Preferred metals include lithium, potassium, calcium, strontium and barium. Combinations of two or more of these metals may be employed. The preferred level of ion-exchange of these materials is rather low. One highly preferred adsorbent is a sodium form 13X zeolite. The same or a different molecular sieve can be used to adsorb the sieve poisons in the guard bed. The molecular sieve used in the guard bed is preferably highly exchanged with the desired cation. A preferred molecular sieve for use in the guard bed is a lithium exchanged X zeolite.

An operational problem related to the adsorptive separation of olefins is the accumulation of certain compounds, present in the feed stream, on the active sites of the adsorbent. These compounds tend to bind so tightly to the sites that the desorption procedure used for olefin recovery does not remove them. They thus render these cites unusable for adsorption of the intended olefin. These compounds are often referred to as adsorbent poisons. As the deleterious effects grow due to the accumulation of more poison from the feed stream, the capacity of the adsorbent and thus the overall process is decreased. The composition of such poisons can vary, with the most common ones encountered in the subject process being diolefins and aromatic hydrocarbons. These include aromatic hydrocarbons containing a hetero atom such as sulfur or oxygen either in their ring structure or in alkyl side chains. Higher molecular weight aromatics are greater poisons. Specific examples of compounds which are considered as poisons in the preferred embodiment of the invention include benzene, toluene, other alkylated benzenes, butadiene, xylenes, ethylbenzene, tetralines, indanes, alkylated-dinaphthalenes, and bi phenyles. Other poisons include aniline, the cresols, pyridine, decaline and tetralin; oxygenates such as phenols, naphthenophenols, napthols, benzofurans and dibenzofurans; nitrogen compounds such as pyroles, pyridines, indoles naphtheno-pyridenes and carbazoles; and sulfur compounds such as benzothiophene, sulfolane, dimethyl benzothiophene, thiophene and benzenthiol.

It is an objective of the invention to provide a method for removing aromatic hydrocarbons from molecular sieve adsorbents used in a guard bed to an adsorptive separation process. It is also an objective to provide such a method which is highly compatible with the desorbents and equipment already used in a simulated moving bed process for olefin separation.

The art has recognized that it is desirable to prevent poisons from deactivating the molecular sieves used to separate olefins as shown by the process described in the previously cited U.S. Pat. No. 5,300,715. In this process a selective aromatics removal zone is employed to prevent the entrance of aromatics into the adsorptive separation zone. It is stated in the patent that the aromatics removal zone can employ a regenerable adsorbent such as a molecular sieve. The reference also describes in general terms that the adsorbent of this zone can be regenerated as by use of liquid benzene. It is not desirable to use benzene as a regenerant in the subject process as small amounts of benzene will unavoidably remain in the guard bed and migrate downstream to the main adsorptive separation zone causing deactivation of the sieves in this zone.

The subject rejuvenation procedure comprises first removing the olefin-containing feed stream from the void volume of the molecular sieve in the guard bed, the internal volume of transfer lines and associated parts of the vessel. At this time the flow of the feed stream will be diverted to another quantity of molecular sieve in a different vessel or possibly stopped if the process employs only one guard bed. This is feasible if the feed stream is flowing into a storage tank rather than directly into a separation zone. The feed stream is flushed from the sieve by a passing a stream of the desorbent through the desorbent bed. This stream is substantially aromatic free and is already available within the process. This step is preferably performed at conditions similar to the normal operating conditions of the guard bed being treated. This flushing step is performed only as long as is needed to substantially remove the residual feed stream from the guard bed. The guard bed effluent stream formed by this step is passed into the raffinate column already employed in SMB type adsorptive separation units. This column is used in the process to separate the raffinate (unadsorbed) and desorbent compounds found in the raffinate stream removed from the adsorption zone. The recovered desorbent may then be recycled and the raffinate compounds discharged from the separation zone without additional equipment. As all of the compounds in the void volume of the guard bed will typically be in the same boiling point range as the raffinate compounds, all of the void volume material will be concentrated into the raffinate stream. The olefins present in the void volume material will be lost to the adsorption process but will not be discarded from the overall process. Often the recovered raffinate is recycled to the process unit, such as a dehydrogenation unit, which produces the feed stream to the adsorptive separation unit. None of the compounds present in the void volumes of the guard bed are lost by rejection to an outside destination. The purge step preferably comprises passing between about 1 to 3 bed volumes of liquid through the guard bed.

In the next step of the process the adsorbent in the guard bed is actually regenerated by driving the aromatic hydrocarbons which have accumulated from the feed to the separation unit, off of the adsorbent. This is performed by continuing the flow of the desorbent stream through the guard bed. However the effluent of the guard bed is diverted and does not flow into the raffinate column. The effluent could be sent to an external separation and recovery zone but is preferably passed into a fractional distillation column added to the process for the purpose of separating the desorbent compounds from the removed aromatics. This regeneration step can be performed at the normal adsorption conditions employed in the guard bed which preferably include a temperature between about 30 and 170° C. The regeneration step is carried for a time sufficient to allow at least 2 and preferably between 5 and 12 volumes of desorbent liquid to pass through the guard bed. At this point the flow of feed stream into the guard bed can be resumed. This points out another advantage of the invention, which is that there is no need to remove the regenerant from the guard bed after the regeneration step. In contrast it would be highly undesirable to resume use of a guard bed filled with benzene, which is suggested in the cited reference as a suitable regeneration media. Benzene is a mild adsorbent poison which will accumulate on the adsorbent and will adversely affect the performance of the separation process. In the subject process there is no need to flush the regenerant from the guard bed. However, as the void volume of the guard bed is filled with desorbent the initial flow from the guard bed (when placed on stream) will contain a high concentration of desorbent. The first few bed volumes of liquid removed from the regenerated guard bed may therefore be passed into the raffinate column to allow recovery of the desorbent. This eliminates a large quantity of desorbent entering the main chamber and disturbing the process. The initial effluent of the newly regenerated guard bed may be passed into any fractionation column in the process which recovers the desorbent.

The use of the desorbent stream as a regenerant media is made possible by the use of a guard bed adsorbent of the appropriate strength. A strong adsorbent requires use of a strong desorbent such as benzene or some adjustment of operating conditions such as a higher temperature. In the subject process it is preferred that an aluminosilicate molecular sieve is employed as an active component of the guard bed adsorbent. A different adsorbent may be employed in the main adsorption zone of the separation process. It preferred to use a guard bed adsorbent comprising zeolite X, with a lithium exchanged zeolite X being highly preferred due to its suitability to the subject process. Such a zeolite would contain from about 0.5 to about 3.0 wt percent lithium.

The operation of the subject process can be discerned by reference to the drawings which is a simplified process flow diagram showing the use of two swing bed guard beds to purify the feed stream to a simulated moving bed process.

Referring now to the drawing, a feedstream produced in a dehydrogenation process and comprising an admixture of normal paraffins and normal olefins having the same molecular weight as the normal paraffins enters the process through line 1. The feedstream is passed into one of the two guard beds 4 and 21 through a manifold system. At the time depicted in the drawing the feedstream of line 1 flows through line 3 into the upper end of the guard bed 4 and then passes through a bed of molecular sieve adsorbent retained within the guard bed. The guard bed selectively adsorbs aromatic hydrocarbons having one or two rings. These aromatic hydrocarbons are present in the feedstream typically at a low concentration less than about 4000–6000 ppm and possibly less than 100 ppm. Therefore substantially all of the entering feedstream passes through the guard bed and emerges through line 5. The feedstream is then transferred to line 6 which carries it to the much larger main adsorptive separation chamber 7.

The adsorptive separation chamber 7 represents the multibed systems typically employed in simulated moving bed operations. These systems comprise from about 10 to about 30 subbeds divided by fluid collection and distribution grids which also serve as points for feeding process streams to the zone and for removing process streams from the adsorption zone. There is therefore at least one separate point for the addition or withdrawal of fluid for each of the multiple subbeds of such a system. The location at which the feedstream is passed into the adsorption chamber 7 and the various other streams are fed into or removed from the adsorption chamber are incrementally moved along the length of the chamber in a manner described in detail in the cited references. This gradual movement of these feed and withdrawal points coupled with the use of a pumparound stream carried by line 11 results in a highly effective simulation of the continuous countercurrent passage of the feedstream through a bed of adsorbent and the continuous removal of raffinate and extract streams. The raffinate stream comprises the unadsorbed components of the feedstream plus a varying amount of desorbent materials picked due to their presence in the void volume of the adsorbent beds of zone 7. The raffinate stream is removed from the adsorption zone 7 through line 10 and passed via line 25 into a raffinate column 26, which separates the raffinate components and the desorbent components. The desorbent is recovered as an overhead stream through line 27 and the raffinate components are recovered as a bottom stream through line 28. The raffinate stream of line 28 may be recycled to the dehydrogenation zone which generates the feed stream of line 1.

In an adsorptive separation process either the rafffinate stream or the extract stream may contain those compounds which are considered the important product of the process. In the subject process the olefinic hydrocarbons of the feedstream are in the intended product and are retained upon the adsorbent located in the adsorption chamber 7. These adsorbed olefins are removed from the adsorbent by a stream of desorbent material fed into a different point of the adsorption zone 7 through line 8. Passage of the desorption stream through the loaded molecular sieve or other adsorbent of the adsorption zone 7 causes the formation of an extract stream carried by line 9. This stream is removed at yet another point in the adsorbent chamber 7. The extract stream comprises an admixture of the olefinic hydrocarbons removed from the feedstream plus a varying amount of desorbent compounds. This admixture is passed through line 9 into the extract column 12. In the extract column the entering admixture of desorbent material and olefinic hydrocarbons is separated by fractional distillation into a bottom stream which comprises the product olefinic hydrocarbons which is removed through line 13 and an overhead stream comprising the desorbent compounds. Preferably the desorbent compounds are a lower molecular weight olefin. The desorbents recovered in this manner are removed in line 14 and divided between a portion passed into line 16 for regeneration of the guard bed and a larger portion withdrawn through line 15. The material in line 15 along with that of line 27 would typically be passed into line 8 as the desorbent of the process but is shown directed to an external source to represent the passage of the overhead material to the storage and distribution systems required for operation of the process.

While the adsorbent in the guard bed 4 is being used to treat the feedstream, the adsorbent in guard bed 21 may be regenerated. It is expected that the length of time required for regeneration will be much shorter than the length of time that the adsorbent bed can be employed for treating the feedstream. The useful cycle length of the adsorbent bed in either of the guard beds 4 and 21 may be adjusted by modifying the amount of molecular sieve in the guard bed. The size of the guard beds and the flow rates of the regenerant streams may therefore be adjusted to optimize the economics of the regeneration. During the regeneration a stream of desorbent material is passed through line 16 into the same manifold system which diverts the feedstream. The desorbent stream of line 16 will flow through manifold lines 20 into the guard bed 21. Passage of the desorbent material through the molecular sieve will first tend to purge liquid from the void volume of the molecular sieve bed and other void volumes of the associated vessel and lines. This will form a flush stream carried by lines 22 into line 23. The effluent stream of the guard bed being regenerated will initially comprise an admixture of the desorbent material used as regenerant plus the material retained in the void volume of the guard bed. As the material in the guard bed is feedstream material, it has significant value since it contains the desired olefins. It also contains paraffins which may be recycled to the dehydrogenation zone. It is therefore undesirable to reject this material and it is passed into line 24 which carries it to line 25 for passage into the raffinate column 26. Substantially all of the feedstream contained within the guard bed which is being regenerated may therefore be captured. Adsorptive separation such as performed in the subject process is typically employed when separation by fractional distillation is impractical due to the variety of the compounds or the closeness of boiling points. In the subject example the olefins and paraffins of the feedstream have similar boiling points and will both pass into the raffinate stream of line 28.

The flush step which allows recovery of the feedstream components as just described is only carried on for a short time. Continued passage of the desorbent through the guard bed will begin to remove the retained aromatic compounds accumulated on the adsorbent bed. It is undesired to pass these materials into the raffinate column. Therefore, the effluent stream of the guard bed being regenerated is diverted from line 24 to line 30. The effluent of the guard bed undergoing the regeneration step is therefore passed through line 30 into an additional fractional distillation column 29 designed and operated under conditions which allow for separation of the entering hydrocarbons into a stream of desorbent material removed as an overhead stream in line 31 and a net bottoms stream comprising the aromatic impurities carried by line 32. After the guard bed has achieved a sufficient degree of regeneration, as determined by analysis of the effluent stream or by a simple timing and measurement of the flow rate of the desorbent material, flow of the desorbent material through the guard bed may be terminated. The quantity of material charged to the fractionation column 29 is therefore expected to be quite small. The composition of the material charged to column 29 and also to the columns 12 and 26 will tend to vary with time due to carryover of void volume material. It is therefore customary to employ surge and mixing drums which tend to stabilize the composition of the feedstream to the columns. These optional items are not shown on the Drawing.

The process shown in the Drawing is subject to considerable variation. For instance, the adsorption zone or chamber 7 could comprise two or more separate multibed chambers employed in a simulated moving bed operation. Alternatively, the adsorbent chamber 7 could comprise a plurality of adsorbent beds operated in a swing bed mode. Furthermore, there is no requirement that two guard beds are employed in the process. The subject process can be employed with a single guard bed or with three or more guard beds. The adsorption chamber 7 can also comprise different forms of adsorbent-feed contact such as true moving bed systems or even a fluidized bed adsorptive separation system.

The subject process has been described as applied to a process for the adsorptive separation of olefins and paraffins. The technique for separating the olefins and paraffins is not believed governing to the application of the subject process as it basically relates to methods of regenerating the guard beds which prepare a feedstream for a separation step. The separation zone or adsorbent chamber 7 could therefore be replaced by other forms of separation such as a crystallization zone, or a liquid-liquid-separation zone.

A preferred embodiment may be therefore characterized as a simulated moving bed process for the separation of linear olefinic hydrocarbons from a feed stream comprising linear olefinic hydrocarbons and other types of hydrocarbons, which process comprises contacting the feed stream with a bed of a molecular sieve under conditions which cause the selective retention of olefinic hydrocarbons on the molecular sieve and the resultant formation of a raffinate stream which is passed into a raffinate column, recovering the retained olefinic hydrocarbons from the molecular sieve by contacting the molecular sieve with a desorbent, characterized in that a guard bed is used to remove aromatic hydrocarbons from the feed stream is periodically regenerated in a procedure which comprises first purging the guard bed by passing a regeneration stream comprising the desorbent through the guard bed while passing the effluent of the guard bed into the raffinate column to recover feed stream components, and then continuing to pass the regeneration stream through the guard bed and passing the effluent of the guard bed into a desorbent recovery column. Some time after the regeneration of this guard bed is completed the guard bed is again placed into use treating additional quantities of feed stream. The flow of the feed stream is restarted and the flow of the newly regenerated guard bed is passed into the raffinate column and then switched into the main bed of molecular sieve.

What is claimed:

1. A process for the separation of a first hydrocarbon from a feed stream comprising said first hydrocarbon and at least one other hydrocarbon, which process comprises periodically regenerating a molecular sieve guard bed used in the process by purging the feed stream from the guard bed using a liquid phase stream of a desorbent used in the separation process and passing the effluent of the guard bed into a fractionation column used in the process to separate the desorbent and raffinate compounds, and then continuing to pass the liquid phase stream of the desorbent through the guard bed but directing the effluent of the guard bed to a desorbent recovery fractionation column.

2. The process of claim 1 wherein the molecular sieve used in the guard bed is an aluminosilicate of different composition than an adsorbent used to perform the separation.

3. The process of claim 1 wherein the desorbent comprises an olefinic hydrocarbon.

4. The process of claim 3 wherein the guard bed is used to remove aromatic hydrocarbons from a feed stream processed in the adsorptive separation process.

5. The process of claim 3 wherein the molecular sieve used in the guard bed is a lithium exchanged type X zeolite.

6. A method for preventing a poison for a molecular sieve adsorbent used in a continuous adsorptive separation process from entering the process, which method comprises;

a.) contacting a feed mixture for the separation process and comprising said adsorbent poison with a guard bed comprising a molecular sieve which adsorbs the adsorbent poison;

b.) periodically purging the guard bed by passing a liquid phase process stream comprising a desorbent compound used in the separation process through the guard bed and passing the effluent of the guard bed into a raffinate column used in the separation process to separate raffinate compounds and desorbent compounds; and, c.) regenerating the molecular sieve contained in the guard bed by passing an additional quantity of the liquid process stream through the guard bed and passing the effluent of the guard bed into a different fractionation column, which column recovers the desorbent compound from the effluent of the guard bed.

7. The process of claim 6 wherein the molecular sieve used in the guard bed comprises a lithium exchanged X zeolite.

8. The process of claim 6 wherein after step (c) is completed the flow of the feed mixture to the now regenerated guard bed is restarted and the initial effluent of the regenerated guard bed is passed into the raffinate column.

9. A simulated moving bed process for the separation of linear olefinic hydrocarbons from a feed stream comprising linear olefinic hydrocarbons and other types of hydrocarbons, which process comprises contacting the feed stream with a bed of a molecular sieve under conditions which cause the selective retention of olefinic hydrocarbons on the molecular sieve and the resultant formation of a raffinate stream which is passed into a raffinate column, and recovering the retained olefinic hydrocarbons from the molecular sieve by contacting the molecular sieve with a desorbent, characterized in that a guard bed is used to remove aromatic hydrocarbons from the feed stream is periodically regenerated in a liquid phase procedure which comprises first purging the guard bed by passing a regeneration stream comprising the desorbent through the guard bed while passing the effluent of the guard bed into the raffinate column to recover feed stream components, and then continuing to pass the regeneration stream through the guard bed and passing the effluent of the guard bed into a desorbent recovery column.

10. The process of claim 9 wherein the desorbent comprises an olefinic hydrocarbon of lower molecular weight than the retained olefinic hydrocarbon.

11. The process of claim 9 wherein the molecular sieve is a lithium exchanged X zeolite.

12. The process of claim 9 wherein after the regeneration of the guard bed is completed the flow of feed stream through the guard bed is restarted and the flow of the effluent of the guard bed is passed into the raffinate column and then switched into the bed of molecular sieve.

* * * * *